(12) United States Patent
Al-Qaisi et al.

(10) Patent No.: US 11,007,080 B2
(45) Date of Patent: May 18, 2021

(54) SYSTEM AND METHOD FOR CUTTING A FLAP USING POLARIZATION SENSITIVE OPTICAL COHERENCE TOMOGRAPHY

(71) Applicant: Alcon Inc., Fribourg (CH)

(72) Inventors: Muhammad Al-Qaisi, Ladera Ranch, CA (US); Craig Bender, Laguna Niguel, CA (US)

(73) Assignee: Alcon Inc., Fribourg (CH)

( * ) Notice: Subject to any disclaimer, the term of this patent is extended or adjusted under 35 U.S.C. 154(b) by 275 days.

(21) Appl. No.: 15/868,125

(22) Filed: Jan. 11, 2018

(65) Prior Publication Data

US 2018/0214309 A1 Aug. 2, 2018

Related U.S. Application Data

(60) Provisional application No. 62/452,101, filed on Jan. 30, 2017.

(51) Int. Cl.

| A61F 9/00 | (2006.01) |
|---|---|
| A61F 9/008 | (2006.01) |
| A61B 3/10 | (2006.01) |
| G01B 9/02 | (2006.01) |
| A61B 90/00 | (2016.01) |

(52) U.S. Cl.
CPC .......... *A61F 9/00836* (2013.01); *A61B 3/102* (2013.01); *A61F 9/0084* (2013.01); *G01B 9/02011* (2013.01); *G01B 9/02091* (2013.01); *A61B 2090/3735* (2016.02); *A61F 2009/00851* (2013.01); *A61F 2009/00872* (2013.01); *A61F 2009/00878* (2013.01); *A61F 2009/00897* (2013.01)

(58) Field of Classification Search
CPC ............... A61F 9/00836; A61F 9/0084; A61F 2009/00851; A61F 2009/00872; A61F 2009/00878; A61F 2009/00897; A61B 3/102; A61B 2090/375; G01B 9/02011; G01B 9/02091
USPC ............................................................ 606/5
See application file for complete search history.

(56) References Cited

U.S. PATENT DOCUMENTS

| 5,411,511 A * | 5/1995 | Hall ...................... A61F 9/0133 606/166 |
|---|---|---|
| 5,822,035 A * | 10/1998 | Bille ........................ A61B 3/10 351/215 |

(Continued)

*Primary Examiner* — Carl H Layno
*Assistant Examiner* — Michael J Lau (57) ABSTRACT

The present disclosure provides a system and method for cutting a flap in laser ophthalmic surgery using polarization sensitive optical coherence tomography (PS-OCT). The system includes a PS-OCT system, a femtosecond laser, control device, and processor. The PS-OCT system includes a PS-OCT source, a polarization component, a reference reflector, a beam splitter, a wave plate, and a detector. The processor receives data relating to an interference pattern of a reflected PS-OCT beam, received at the detector, determines a relative fiber orientation of the sample, determines whether a photodisruption pattern generated by the femtosecond laser to cut the flap should be adjusted horizontally or vertically, based on the relative fiber orientation, and may generate a control signal to adjust the photodisruption pattern generated by the femtosecond laser. The disclosure further provides a method for cutting a flap on an eye using PS-OCT.

17 Claims, 7 Drawing Sheets

(56) References Cited

U.S. PATENT DOCUMENTS

| | | | | |
|---|---|---|---|---|
| 6,208,415 | B1* | 3/2001 | De Boer | G01N 21/4795 356/450 |
| 6,325,792 | B1* | 12/2001 | Swinger | A61F 9/00804 606/11 |
| 7,418,169 | B2* | 8/2008 | Tearney | A61B 1/00082 385/11 |
| 7,733,497 | B2* | 6/2010 | Yun | G02B 6/3604 356/497 |
| 7,742,173 | B2* | 6/2010 | Yun | G01N 21/4795 356/479 |
| 8,804,126 | B2* | 8/2014 | Tearney | A61B 5/0075 356/479 |
| 2002/0111607 | A1* | 8/2002 | Bille | A61F 9/00827 606/5 |
| 2003/0100893 | A1* | 5/2003 | Bille | A61F 9/008 606/4 |
| 2005/0171438 | A1* | 8/2005 | Chen | A61B 5/7203 600/476 |
| 2007/0177152 | A1* | 8/2007 | Tearney | A61B 5/0084 356/477 |
| 2008/0007734 | A1* | 1/2008 | Park | A61B 5/0066 356/495 |
| 2008/0180683 | A1* | 7/2008 | Kemp | G01B 9/02072 356/491 |
| 2008/0291463 | A1* | 11/2008 | Milner | A61B 1/00167 356/491 |
| 2009/0073387 | A1* | 3/2009 | Meyer | A61B 3/12 351/246 |
| 2009/0171327 | A1* | 7/2009 | Kurtz | A61F 9/00838 606/6 |
| 2010/0324542 | A1 | 12/2010 | Kurtz | |
| 2012/0203215 | A1* | 8/2012 | Riedel | A61F 9/008 606/5 |
| 2012/0327423 | A1 | 12/2012 | Hanebuchi | |
| 2013/0100456 | A1* | 4/2013 | Yu | G01B 9/02082 356/479 |
| 2013/0110095 | A1* | 5/2013 | Boxer Wachler | A61F 9/00836 606/5 |
| 2014/0171926 | A1* | 6/2014 | Depfenhart | A61F 9/0079 606/4 |
| 2014/0343411 | A1* | 11/2014 | O'Brien | A61B 5/7257 600/425 |
| 2015/0055137 | A1* | 2/2015 | Brown | G01B 9/02091 356/479 |
| 2015/0230701 | A1* | 8/2015 | Sato | A61B 3/0025 351/206 |
| 2016/0198939 | A1* | 7/2016 | Fukuhara | A61B 3/113 351/206 |
| 2016/0206373 | A1* | 7/2016 | Chen | A61B 5/0036 |
| 2016/0305762 | A1* | 10/2016 | Suter | G01B 9/02011 |
| 2016/0320171 | A1* | 11/2016 | Hanebuchi | G01B 9/02028 |
| 2017/0100234 | A1* | 4/2017 | Culbertson | A61F 2/16 |

* cited by examiner

SYSTEM AND METHOD FOR CUTTING A FLAP USING POLARIZATION SENSITIVE OPTICAL COHERENCE TOMOGRAPHY

TECHNICAL FIELD

The present disclosure relates to optical coherence tomography ("OCT"), and more specifically, to systems and methods for cutting a flap in ophthalmic surgery, using data generated by polarization sensitive optical coherence tomography ("PS-OCT").

BACKGROUND

In ophthalmology, ophthalmic surgery is performed on the eye and accessory visual structures to save and improve the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in precision or accuracy of surgical techniques can make a tremendous difference in the patient's vision after the surgery.

One type of ophthalmic surgery, refractive eye surgery, is used to correct a variety of vision problems. One common type of refractive surgery is known as LASIK (laser-assisted in situ keratomileusis) and is used to correct myopia and hyperopia, astigmatism, or more complex refractive errors. Other ophthalmic surgeries may correct corneal defects or other problems. For instance, phototherapeutic keratectomy ("PTK") may be used to remove diseased corneal tissue or corneal irregularities either alone or in combination with LASIK. Another common ophthalmic surgery is the removal of cataracts.

During LASIK, PTK, cataract surgery, and other ophthalmic surgeries, corrective procedures are commonly performed on interior parts of the eye, such as the corneal stroma or the lens, rather than on the eye surface. This practice tends to improve surgical outcomes by allowing the corrective procedure to be targeted to the most effective part of the eye, by keeping the outer, protective parts of the cornea largely intact, and for other reasons.

The interior part of the eye may be accessed in a variety of manners, but frequently access involves cutting a flap in the cornea or otherwise cutting the cornea. Corneal cutting is often performed by a femtosecond laser that uses photodisruption to create incisions, eliminating collateral damage of surrounding tissues associated with slower lasers and complications associated with mechanical cutting instruments, such as blades. The pulsed nature of the femtosecond laser causes it to vaporize corneal tissue in an interspersed pattern, corresponding to the location of the beam focus when the laser is pulsed on, leaving intact corneal tissue corresponding to the location of the beam focus when the femtosecond laser is off between pulses. Typically the pulsed femtosecond laser is only on for a very short pulse time. The beam focus then moves to a new location within the cornea before the femtosecond laser is pulsed on again. This produces a series of small photodisruptions, typically a few micrometers in average size. The small photodisruptions are typically also spaced a few micrometers apart. The interspersed pattern (a "photodisruption pattern") thus formed is such that the corneal tissue is effectively cut, allowing, for instance, the flap to be detached and lifted, while decreasing damage to the corneal tissue by the femtosecond laser.

Femtosecond lasers can therefore be used to dissect tissue on a microscopic level. When cutting a flap, it is important for the surgeon to have additional information about the tissues to be cut and internal structures of the eye that cannot effectively be seen using only the surgical microscope.

SUMMARY

The present disclosure provides a system for cutting a flap in a cornea of an eye using PS-OCT, which includes a PS-OCT system, a processor, and a femtosecond laser operable to generate a photodisruption pattern to cut a flap in a sample in the cornea of the eye, and connected to a control device operable to adjust the photodisruption pattern generated by the femtosecond laser. The PS-OCT system includes a PS-OCT source operable to generate a PS-OCT source beam, a polarization component operable to control a polarization of the PS-OCT source beam, and a beam splitter. The beam splitter is operable to split the PS-OCT source beam into a sample beam that travels along a sample arm until it is reflected by a sample to form a reflected sample beam, and a reference beam that travels along a reference arm until it is reflected by the reference reflector to form a reflected reference beam, and operable to combine the reflected sample beam and the reflected reference beam to form a reflected PS-OCT beam. The PS-OCT system further includes a wave plate on the sample arm, the wave plate operable to convert the sample beam into polarized light with a known polarization state such that a polarized sample beam is incident upon the sample. The PS-OCT system further includes a detector operable to receive the reflected PS-OCT beam, detect an interference pattern of the reflected PS-OCT beam, and generate data relating to the interference pattern. The processor is operable to receive data relating to the interference pattern of the reflected PS-OCT beam, determine a relative fiber orientation of the portion of the sample reflecting the sample beam, based on a birefringence properties of the portion of the sample, determine whether the photodisruption pattern should be adjusted horizontally or vertically based on the relative fiber orientation and fiber density of the portion of the sample, generate a control signal operable to adjust the photodisruption pattern horizontally or vertically when it is determined that the photodisruption pattern should be adjusted, and transmit the control signal to the control device connected to the femtosecond laser.

In additional embodiments, which may be combined with one another unless clearly exclusive: the polarizer is a vertical polarizer or a horizontal polarizer; the detector is a dual-detector system comprising a vertical polarization sensitive detector and a horizontal polarization sensitive detector, and the system further comprises a polarizing beam splitter operable to split the reflected PS-OCT beam into a vertically polarized component and a horizontally polarized component, the vertically polarized component directed to the vertical polarization sensitive detector, and the horizontally polarized component directed to the horizontal polarization sensitive detector; the detector is a single-detector system comprising a combined horizontal polarization sensitive and vertical polarization sensitive detector; the processor is further operable to determine whether the relative fiber orientation of the sample is lower than a user-specified threshold, and generate the control signal to adjust the photodisruption pattern when the relative fiber orientation is lower than the user-specified threshold; the processor is further operable to determine a relative fiber density of the portion of the sample reflecting the sample beam, based on the birefringence properties of the portion of the sample, determine whether the relative fiber density is lower than a user-specified threshold, and generate the control signal to adjust the photodisruption pattern when the relative fiber density is lower than the user-specified threshold; the control signal to adjust the photodisruption pattern does not cause the depth of the flap to be less than a user-specified minimum depth required to create a functional flap; and the processor is further operable to generate and transmit a pictorial representation of the portion of the sample reflecting the polarized sample beam, and wherein the system further comprises a display operable to present the pictorial representation.

The present disclosure further provides a method for cutting a flap in a cornea of an eye using polarization sensitive optical coherence tomography (PS-OCT). The method includes receiving, at a detector of a PS-OCT system, an interference pattern of a reflected PS-OCT beam, the reflected PS-OCT beam comprising a combined reflected sample beam and a reflected reference beam, the reflected sample beam reflected by a portion of a sample in the cornea of the eye, and the reflected reference beam reflected from a reference reflector, determining a relative fiber orientation of the portion of the sample that reflected the sample beam, based on a birefringence properties of the portion of the sample, determining whether a photodisruption pattern generated by a femtosecond laser to cut the flap in the sample should be adjusted horizontally or vertically, based on the relative fiber orientation, generating a control signal operable to adjust the photodisruption pattern horizontally or vertically when it is determined that the photodisruption pattern should be adjusted, and transmitting the control signal to a control device connected to the femtosecond laser, the control device operable to adjust the photodisruption pattern.

In additional embodiments, which may be combined with one another unless clearly exclusive: the detector of the PS-OCT system is a dual-detector system comprising a vertical polarization sensitive detector and a horizontal polarization sensitive detector, and the PS-OCT system further comprises a polarizing beam splitter operable to split the reflected PS-OCT beam into a vertically polarized component and a horizontally polarized component, the vertically polarized component directed to the vertical polarization sensitive detector, and the horizontally polarized component directed to the horizontal polarization sensitive detector; the detector of the PS-OCT system is a single-detector system comprising a combined horizontal polarization sensitive and vertical polarization sensitive detector; the method further comprises determining whether the relative fiber orientation is lower than a user-specified threshold, and generating the control signal to adjust the photodisruption pattern when the relative fiber orientation is lower than the user-specified threshold; the method further comprises determining a relative fiber density of the portion of the sample reflecting the sample beam, based on the birefringence properties of the portion of the sample, determining whether the relative fiber density is lower than a user-specified threshold, and generating the control signal to adjust the photodisruption pattern when the relative fiber density is lower than the user-specified threshold; the control signal to adjust the photodisruption pattern does not cause the depth of the flap to be less than a user-specified minimum depth required to create a functional flap; and the method further comprises generating a pictorial representation of the portion of the sample that reflected the sample beam, and transmitting the pictorial representation to a display.

The above systems may be used with the above methods and vice versa. In addition, any system described herein may be used with any method described herein and vice versa.

BRIEF DESCRIPTION OF THE DRAWINGS

For a more complete understanding of the present invention and its features and advantages, reference is now made to the following description, taken in conjunction with the accompanying drawings, which are not to scale, in which like numerals refer to like features, and in which.

DETAILED DESCRIPTION

In the following description, details are set forth by way of example to facilitate discussion of the disclosed subject matter. It should be apparent to a person of ordinary skill in the field, however, that the disclosed embodiments are exemplary and not exhaustive of all possible embodiments.

The disclosed systems and methods are for cutting a flap in the cornea of an eye using data generated by PS-OCT. The system includes a PS-OCT system, a femtosecond laser that generates a photodisruption pattern and control device that can adjust the photodisruption pattern generated by the femtosecond laser, and a processor. The PS-OCT system includes a PS-OCT source that generates a PS-OCT source beam, a polarization component, a reference reflector, a beam splitter, a wave plate, and a detector. The processor receives data relating to an interference pattern of a reflected PS-OCT beam, received at the detector, determines a relative fiber orientation of a portion of the sample (based on birefringence properties of the portion of the sample), and determines whether the photodisruption pattern generated by the femtosecond laser should be adjusted horizontally or vertically based on the relative fiber orientation of the portion of the sample reflecting the sample beam. As used herein with respect to an eye, "horizontal" refers to the X and Y-directions in the X-Y plane, defined as the plane roughly perpendicular to the apex of the cornea, and "vertical" refers to the Z-direction in the Z-plane, defined as the plane roughly perpendicular to the X-Y plane. The processor may generate a control signal to adjust the photodisruption pattern generated by the femtosecond laser horizontally or vertically, when it is determined that the photodisruption pattern should be adjusted. This control signal may be transmitted to the control device connected to the femtosecond laser to adjust the photodisruption pattern.

The disclosure further provides a method for cutting a flap in the cornea of an eye using PS-OCT. The method includes first receiving, at a detector of a PS-OCT system, an interference pattern of a reflected PS-OCT beam, the reflected PS-OCT beam comprising a combined reflected sample beam and a reflected reference beam, the reflected sample beam reflected by a sample, and the reflected reference beam reflected from a reference reflector. The method further includes determining a relative fiber orientation of a portion of the sample that reflected the sample beam (based on birefringence properties of the portion of the sample), determining whether a photodisruption pattern generated by a femtosecond laser to cut a flap on the sample should be adjusted horizontally or vertically, based on the relative fiber orientation, generating a control signal operable to adjust the photodisruption pattern horizontally or vertically when it is determined that the photodisruption pattern should be adjusted, and transmitting the control signal to a control device connected to the femtosecond laser, the control device operable to adjust the photodisruption pattern.

PS-OCT is a functional imaging method that is an extension of OCT. PS-OCT provides additional contrast and tissue discrimination (in relation to traditional OCT methods that only measure reflectivity) by additionally using the light polarizing properties of a sample to discern further information relating to the sample. The sample may be a biological sample, such as a human eye. PS-OCT is based on the concept that some tissues can change the polarization state of incident light. PS-OCT may be used to visualize certain polarization properties of the eye, for instance birefringence, diattenuation, and depolarization. Because several structures or layers of the eye, including the cornea, retinal epithelium, and retinal nerve fiber layer, alter the polarization state of incident light, a PS-OCT image (also referred to herein as a pictorial representation) can present tissue-specific contrast, allowing the user to determine polarization properties such as fiber alignment and fiber density.

PS-OCT may be used to measure tissue birefringence, which is directly related to fiber orientation in tissues. The fiber orientation of corneal tissue is directly relevant to the biomechanical integrity and stability of the cornea. Generally, tissue birefringence is the optical property of a material having a refractive index (light propagation velocity) that depends on the polarization and propagation direction of light. In PS-OCT, tissue birefringence may be determined by measuring the phase retardation of the light incident upon and reflected from the sample, as a function of tissue depth. In a sample, tissue birefringence is often caused by narrow fibrous structures that cannot be resolved by conventional OCT systems. Such OCT systems only account for the intensity of reflected or backscattered light.

Integration of PS-OCT in laser ophthalmic surgery as described herein is advantageous because in many surgical procedures, for example LASIK, it is important to preserve the biomechanical integrity and stability of the cornea because such procedures rely on the corneal tissue to heal with minimal or no post-operative intervention. Accordingly, it is preferable to make incisions in places where the corneal tissue has strong fiber alignment because fiber alignment is essential to the biomechanical integrity and stability of the cornea. Although it may be desirable to cut a flap in tissue that has both strong fiber alignment and density, it may be most preferable to avoid sections where fiber alignment is weak even if those fibers are dense because those sections with weak or compromised fiber alignment will have weak biomechanical stability.

In LASIK surgery, for example, the surgeon first cuts a flap in the anterior surface of the cornea with a femtosecond laser, allowing access to the interior of the eye, and then may perform ablation on the eye with an excimer laser. The flap is often cut as thinly as possible to preserve the biomechanical integrity and stability of the cornea. In most corneal flaps, the femtosecond laser will cut below the epithelium and the Bowman's membrane and include at least some of the corneal lamellae in the cut. The corneal lamellae includes the layers of collagen fibers that make up the corneal stroma. Thus, the flap is preferably cut to include the thinnest amount of the denser cross-linked collagen fibers of the corneal stroma necessary to still create a functional flap. Because the user must be able to peel back a flap to allow sufficient access for the excimer laser, a functional flap must be able to be peeled back without tearing or causing additional trauma to the eye. Further, post-operative healing after creation of a functional flap is limited to regeneration of the epithelial tissue while the posterior corneal topography is maintained. The anterior chamber of the eye is pressurized. Thus, when a flap cut compromises the mechanical integrity of the corneal stroma, the pressure on the posterior cornea will deform the corneal tissue resulting in a poor and unpredictable surgical outcome.

Preserving the biomechanical integrity and stability of the cornea when cutting a flap is a challenge because the density of the corneal lamellae increases toward the anterior surface of the cornea. Thus, the femtosecond laser used to cut the flap must penetrate the dense anterior surface of the cornea with sufficient depth that the surgeon may peel back the flap without it tearing, but also, only with the depth necessary to generate a functional flap while preserving the patient's ability to heal quickly. By implementing PS-OCT, the disclosed systems and methods visualize fiber alignment of the corneal stroma to control corneal flap thickness by determining and adjusting the depth at which the flap is cut.

Current femtosecond lasers can only be programmed to cut a flap at a consistent, pre-determined depth input by the user or determined by the system and docking configuration. Because the flap is cut in a matter of seconds, and the eye is sometimes docked to the system, such systems generally cannot be adjusted while the cut is made. Typically, the entire flap is cut at the programmed depth with only structural feedback provided as to the depth of the cut. Accordingly, such systems are not capable of distinguishing between stromal structures with varying levels of fiber alignment or density.

In contrast, the disclosed systems and methods provide real time visualization of corneal layers to determine those with the highest collagen fiber cross-linking and density. Real time may mean in less than half a second, in less than one second, or otherwise in less than the normal reaction time of a user of visual or auditory information. The data generated by such systems and method may be used, for example, to adjust the femtosecond laser while the flap is being cut. Because PS-OCT scanning may be performed very quickly, for example, generating at least tens of thousands of axial scans per second, such systems and methods may generate data to optimize the flap while it is being created. In this example, PS-OCT may reveal that prior measurements and plans for cutting the flap are not accurate or optimal in view of the fiber orientation or density of the corneal stroma. Further, acute inaccuracies may arise during the procedure, such as eye rotation and changes in patient positioning. When any of these conditions arise, the disclosed systems and methods may adjust the shape of the flap cut, the depth of the flap cut, or may vary the thickness of portions of the flap in view of preserving the biomechanical stability of the corneal tissue.

By adjusting the photodisruption pattern generated by the femtosecond laser to adjust the flap cut, for example, by minimizing the depth of the flap in places where the fibers of the corneal stroma lack alignment or density, the disclosed systems and methods may decrease the risk of post-surgical complications to the patient and improve surgical outcomes. The PS-OCT data generated may be used by a surgeon (1) pre-operatively, (2) during a surgical procedure, and (3) in post-operative analyses. Pre-operatively, data relating to fiber alignment and density may be used to assess whether the patient is a good candidate for laser treatment. The data may also be used to determine the depth of the cut required to create a functional flap, and to determine places where the depth of the flap may be or should be varied to compensate for increased risk of post-surgical complications and difficulty healing due to physical trauma upon the corneal tissue. At the beginning of the procedure, the data may be used to confirm that significant parameters of the eye have not changed since the pre-operative analysis such that the patient is no longer a good candidate for laser treatment. During the procedure, the data may be used to vary the depth of the cut overall or only in certain places to compensate, for example, for errors in pre-operative measurements or errors related to patient movement or misalignment during docking of the femtosecond laser. Post-operatively, the pre-operative PS-OCT images may be compared to subsequently generated PS-OCT images to evaluate whether the cornea is healing properly.

OCT is an interferometric analysis technique for structural examination of a sample that is at least partially reflective to light, such as a biological tissue. OCT systems may be used to determine distance and depth profiles and other information based on interference patterns created by the interaction between a reflected beam from a reference reflector and a reflected beam from a sample.

In an OCT system, a single OCT source beam is split, by a beam splitter, into two component beams, a sample beam that is propagated to and at least partially reflected by a sample, and a reference beam that is propagated to and reflected by a reference reflector. Each component beam is typically reflected back to the beam splitter and combined, although certain OCT systems may not require each reflected beam to return to the beam splitter to be combined. When the reflected sample beam and reflected reference beam are combined, an interference pattern is generated, which may be used to measure distances and depth profiles of the sample and other information and to image internal target structures that the sample beam passed through. In ophthalmic surgery, an OCT system may be used, for example, to provide cross sectional views of the retina in high resolution.

OCT systems generally rely on the intensity of backscattered reflected light. These OCT systems cannot directly differentiate between different types of tissues and have trouble distinguishing between layers of tissues. This is especially problematic when an ocular disease has led to damaged, distorted, displaced, or disrupted retinal layers. Thus, any additional tissue discrimination provided by PS-OCT is of significant value in the diagnosis of ocular diseases, planning of surgical treatments, and performance of such treatments.

By utilizing information carried by polarized light in addition to information carried by reflected light, PS-OCT provides enhanced tissue discrimination and quantitative measurements of sample properties. To measure the polarizing properties of a sample using PS-OCT, the sample is typically illuminated with light of a known polarization state, or illuminated with light at multiple polarization states with known relations. For example, the sample may be illuminated by a bulk optics system or light generated by a PS-OCT source may be propagated to the sample via an optical fiber, which may be a polarization maintaining (PM) fiber. When a PS-OCT light source is used, it generates a PS-OCT source beam, which is first propagated through a polarizing filter of a known polarization. The polarized PS-OCT source beam is then split by a beam splitter into two component beams, a sample beam that is propagated to and at least partially reflected by a sample (the sample arm), and a reference beam that is propagated to and reflected by a reference reflector (the reference arm). Because PS-OCT is polarization sensitive, each component beam may pass through or contact certain wave plates, filters, mirrors, or lenses, depending on the specific PS-OCT configuration. After each component beam is respectively reflected by the sample and the reference reflector, they may be recombined at the beam splitter to form a reflected PS-OCT beam. When the reflected sample beam and the reflected reference beam are recombined, an interference pattern is formed. The reflected PS-OCT beam is directed to a polarization sensitive detector, which detects and generates data relating to the reflected polarized light of the reflected PS-OCT beam. The data may be transmitted to and used by a processor to determine certain polarization properties, such as fiber orientation, of the tissue reflecting the sample beam.

Figure 1:
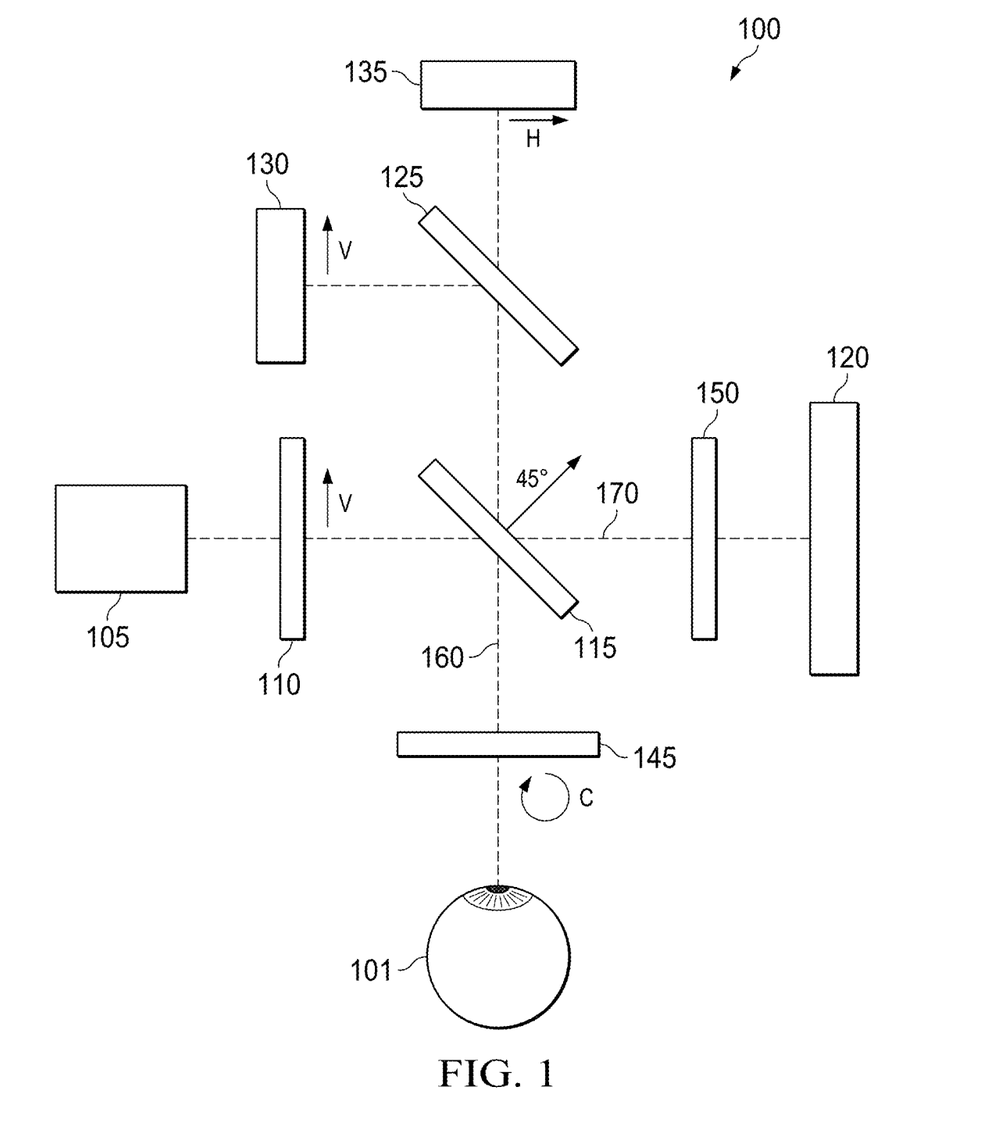
FIG. 1 is a schematic diagram of a PS-OCT system.

Referring now to the figures, FIG. 1 is a schematic diagram of PS-OCT system 100. As shown, PS-OCT system 100 includes PS-OCT light source 105, polarization component 110, beam splitter 115, reference reflector 120, polarizing beam splitter 125, vertical polarization sensitive detector 130, horizontal polarization sensitive detector 135, and wave plate 145. In FIG. 1, system 100 also includes a polarization system 150.

The PS-OCT source 105 generates a PS-OCT source beam, which is propagated through a vertical polarizer 110, to a beam splitter 115. Polarization component 110 may control a polarization of the PS-OCT source beam. As shown, polarization component 110 is a vertical polarizer (hereinafter referred to as vertical polarizer 110, in FIG. 1), and polarization system 150 is a quarter wave plate ("QWP") positioned at 22.5 degrees (described in detail below). The PS-OCT light source may be, for example, a superluminescent diode, a supercontinuum laser, or a swept-source laser. Although labelled as a PS-OCT light source, PS-OCT source 105 may be any light source suitable for OCT imaging. In system 100, any beam of light described may be propagated by optical fibers. For example, light may be propagated by a conventional (non-PM) single-mode fiber and a modulator may be implemented to differentiate between the polarization changes in the tissue and the system. Alternatively, the light may be propagated by a polarization maintaining (PM) fiber, which allows the light to be propagated in two linear orthogonal channels (fast and slow). Each linear channel of orthogonal light is generally perpendicular to the other (i.e., the fast channel is perpendicular to the slow channel).

Upon leaving PS-OCT source 105, the PS-OCT source beam is typically polarized light, which means that it is light generally oscillating in one single plane. In contrast, unpolarized light is light that is oscillating in more than one plane. When the PS-OCT source beam passes through vertical polarizer 110, the transmitted light that reaches beam splitter 115 is vertically polarized, meaning the light is only oscillating in a vertical direction. Vertical polarizer 110 is a type of linear polarizer, another example of which is a horizontal polarizer, in which the transmitted light is only oscillating in a horizontal direction. As applied to linearly polarized light, the terms "vertical" and "horizontal" respectively refer to the direction the wave oscillates in the optical axis in which it is propagated. A linear polarizer may be an absorptive polarizer, which absorbs the unwanted polarization states and transmits the chosen polarization state. For example, a vertical polarizer absorbs unwanted polarization states, including horizontal polarization states, and only transmits vertical polarization states. A linear polarizer may alternatively be a beam-splitting polarizer, which splits the unpolarized light into two component beams, each with an opposite polarization states (i.e., one component beam would have a vertical polarization state and the other, a horizontal polarization state).

Although polarization component 110 is described in FIG. 1 as being a vertical polarizer, polarization component 110 may alternatively be a horizontal polarizer or other polarizer of a known polarization state, although using a vertical or horizontal polarizer may facilitate analysis of data generated relating to a reflected PS-OCT beam. The importance of polarization component 110 is to receive the incident PS-OCT source beam and transmit a polarized PS-OCT source beam with a known polarization. Similarly, the importance of wave plate 145 and polarization system 150 is to receive an incident beam of light and transmit a beam of light with a known polarization, described in detail below. Accordingly, some PS-OCT systems may not include polarization system 150 depending on the system's configuration. For example, polarization system 150 may be not be used when the beam of light leaving the beam splitter on the reference arm is orthogonal, (e.g., the light leaving beam splitter 115 is at a 45 degree angle and wave plate 145 is oriented at 0 degrees with respect to the vertical or horizontal polarization of the light propagated on the sample beam).

When the vertically polarized PS-OCT source beam reaches the beam splitter, it is split into two component beams, a polarized sample beam that is propagated to and at least partially reflected by a sample, and a polarized reference beam that is propagated to and reflected by a reference reflector. The sample beam may be referred to as propagated on sample arm 160, and the reference beam may be referred to as propagated on reference arm 170. As described in detail below, the polarization state of the reference beam is known because optical properties of the reference reflector are known and because the polarization state of the reference beam is known. In FIG. 1, the polarization state of the reference beam is known because the reference beam is converted by means of a polarization system 150, prior to reaching reference reflector, to produce two orthogonal polarization components with equal intensities upon re-entry of the beam splitter. Polarization system 150 may be a QWP, for example, a QWP at 22.5 degrees. Each component beam is typically reflected back to the beam splitter 115 and combined, although certain PS-OCT systems may not require each reflected beam to return to the beam splitter to be combined.

When the sample beam is transmitted along sample arm 160, it passes through wave plate 145 before reaching sample 101. As shown, wave plate 145 is a QWP and sample 101 is a human eye. Wave plate 145 converts the sample beam's linear vertically polarized light to circularly polarized light with a known polarization state. Although system 100 is described as using QWP's, other systems may implement other types of wave plates, for instance a half-wave plate ("HWP") or a full wave plate ("FWP"). A wave plate, which is also called a retarder, is an optical device that alters the polarization state of a light wave passing through it. Specifically, a wave plate is an optically transparent material that resolves a beam of polarized light into two orthogonal components (i.e., at a right angle to each other); retards the phase of one component relative to the other; and recombines the components into a single beam with altered polarization characteristics. For example, a HWP shifts the polarization direction of linearly polarized light and a QWP may convert linearly polarized light to circularly polarized light and vice versa, or may convert linearly polarized light to elliptically polarized light and vice versa. Wave plates are constructed of birefringent material, for instance quartz or mica, which causes the index of refraction to differ based on the different orientations of light passing through it. The optical behavior of a wave plate varies depending on many factors, such as the thickness of the wave plate, the wavelength of incident light and the variation of the index of refraction. For instance, depending on the thickness of the wave plate, light with polarization components along both axes will be transmitted at a different polarization state. By altering these parameters, such wave plates can alter the polarization of incident light by introducing a controlled phase shift between the two polarization components of the light wave.

As shown in FIG. 1, wave plate 145 is positioned at 45 degrees, meaning that the transmission axis of the polarization component (here, vertical polarizer 110) is chosen such that the linearly polarized light incident upon the wave plate is halfway (at a 45 degree angle) between the fast and slow axes of the wave plate 145. Thus, wave plate 145 converts the linear vertically polarized light to circularly polarized light. Similarly, when the reference beam is transmitted along the reference arm 170, it passes through polarization system 150 before reaching reference reflector 120. In FIG. 1, polarization system 150 is a QWP positioned at 22.5 degrees, meaning that the transmission axis of the linearly polarized light is positioned such that the fast and slow axes of the wave plate will differ, causing the light transmitted by polarization system 150 to be elliptical. Polarization system 150 may alternatively be a Faraday rotator, which is a polarization rotator based on the Faraday effect. Generally, a Faraday rotator is able to rotate the polarization state of incident light because one polarization of the incident light is in ferromagnetic resonance with the Faraday rotator material, which causes its phase velocity to be higher than the other.

When each reflected component beam is combined at the beam splitter, they form a reflected PS-OCT beam, and an interference pattern is generated. The reflected PS-OCT beam is directed to a polarizing beam splitter ("PBS") 125. As shown, PBS 125 splits the reflected PS-OCT beam into a component that is vertically polarized and directed to a vertical polarization sensitive detector 130, and a component that is horizontally polarized and directed to a horizontal polarization sensitive detector 135. In other examples, system 100 may implement a single-detector that can detect both reflected PS-OCT light that is vertically polarized and horizontally polarized. A single-detector system may include a combined horizontal polarization sensitive and vertical polarization sensitive detector. Single and dual-detector systems generate relatively similar reflectivity (OCT) and birefringence (PS-OCT) images, respectively.

As shown in FIG. 1, each detector may detect and generate data relating to the interference pattern, and accordingly, the reflected PS-OCT beam. This data may be transmitted to a processor (not shown) and may be processed to generate information about the sample, including the fiber orientation and density of the tissue. Because the fiber orientation and density of the tissue affects the polarization of incident light (here, the sample beam), at least via birefringence, the phase retardation of the reflected sample beam may be determined as a function of tissue depth. This data relating to the phase retardation of the reflected sample beam, in relation to the phase retardation of the reflected reference beam, provides information directly related to the fiber orientation and density of the tissue that the sample beam passed through. Generally, tissue birefringence increases as fiber alignment, orientation and density increase, and as a result, the phase retardation of the reflected sample beam will differ as compared to the reflected reference beam.

The data generated at each of detectors 130 and 135 of system 100 may be transmitted to a processor (not shown) and used, for example, to generate a pictorial representation of the corneal tissue at the portion of the eye 101 that reflected the sample beam. Pictorial representations may be presented on a display, which may be a display screen or a head-up display, for example. Such pictorial representations may indicate the relative fiber orientation and fiber density of the corneal tissue, based on a birefringence properties of the corneal tissue at the portion of the sample reflecting the sample beam. Such pictorial representations may provide user feedback for controlling or adjusting a flap cut manually, for planning a flap cut procedure, or for determining whether a patient is a suitable candidate for such femtosecond laser procedures.

In free-space PS-OCT systems and PM-fiber based PS-OCT systems, the polarization state in the interferometer is maintained. Thus, wave plates are often implemented because the polarization transformations that will happen in the wave plates are known. In contrast, for single-mode fiber systems, there are unknown polarization transformations in the system itself, and therefore wave plates are typically not effective. In such single-mode fiber systems, an alternative approach is to modulate the polarization states of the light and interrogate the tissue at the same place multiple times with different polarizations and reconstruct the data generated in a way that differentiates between the tissue birefringence and the system birefringence.

Though not shown in FIG. 1, additional components may be implemented with system 100. For example, various circular polarizers may be used to create circularly polarized light or alternatively to selectively absorb or transmit clockwise or counter-clockwise circularly polarized light. In another example, additional wave plates, filters, polarization components, polarization systems, mirrors, or lenses may be implemented, depending on the chosen PS-OCT configuration. Also, in single-mode fiber systems, polarization modulators may often be implemented to differentiate between the polarization changes in the tissue and the system.

PS-OCT system 100 of FIG. 1 is an example configuration of a PS-OCT system. Another example PS-OCT configuration may include a PS-OCT light source that generates a PS-OCT source beam that is propagated through a polarization modulator to an interferometer, where it is split into a reference beam directed to a reference and a sample beam directed to the sample, and when the reflected sample and reflected reference beams are combined, they are directed to a detector. Another example PS-OCT configuration may include a PS-OCT light source that generates a PS-OCT source beam that is propagated to an interferometer, where it is split into a reference beam directed to a reference and a sample beam directed to the sample. The reference beam is reflected from the reference and passes through a polarization component that converts the polarization state of the returning reference beam into a polarization state with two equal orthogonal polarization components (i.e., equal vertical and horizontal components). The sample beam passes through a polarization modulator before contacting and being reflected by the sample. Both the reflected sample and reflected reference beams are combined, they are directed to a detector.

Figure 2A:
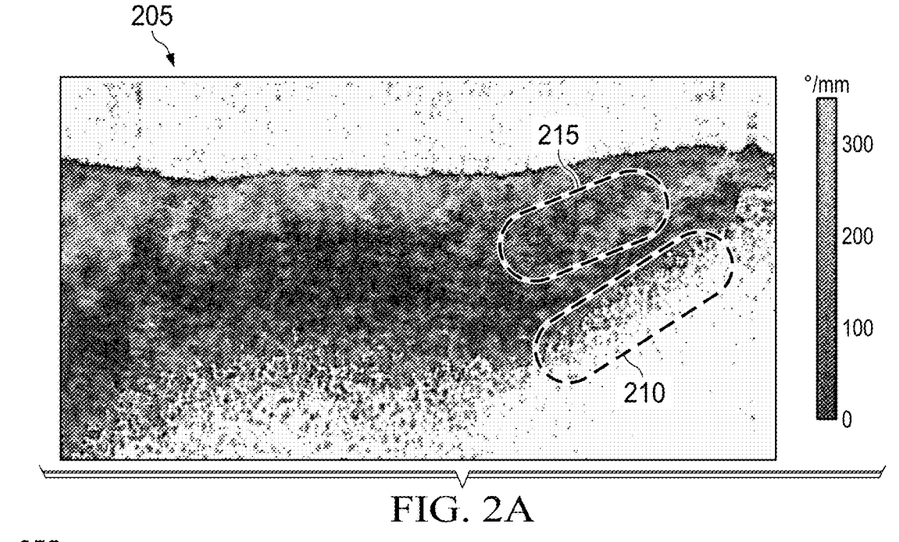
FIG. 2A is a digitally processed image of a porcine iris generated by PS-OCT.
Figure 2B:
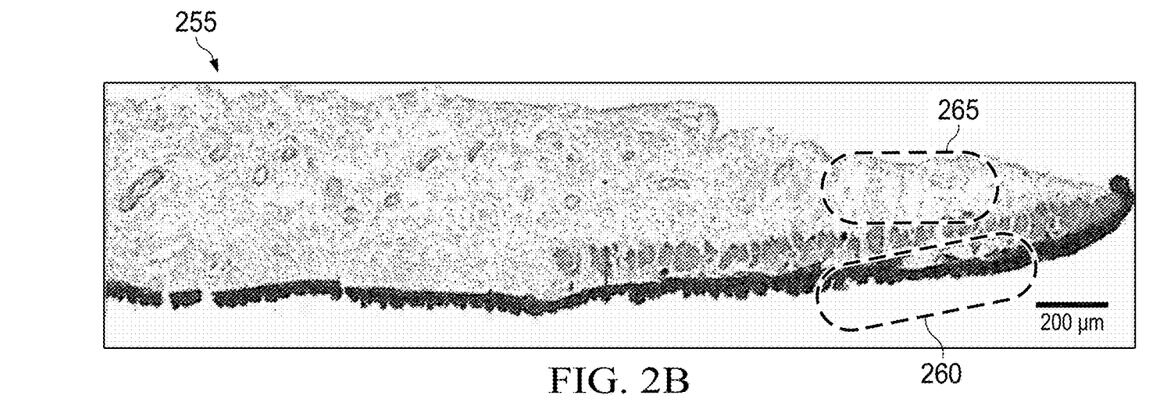
FIG. 2B is a histology image of the same porcine iris imaged in FIG. 2A, the histology image showing the locations of blood vessels in the anterior stroma.

FIG. 2A is a digitally processed image 205 of a porcine iris generated by PS-OCT and FIG. 2B is a histology image 255 of the same porcine iris showing the locations of blood vessels in the anterior stroma. By comparing FIGS. 2A and 2B, these images demonstrate that high fiber alignment results in high local retardance, and low fiber alignment results in low local retardance. Specifically, at position 260 in FIG. 2, the collagen fibers of the anterior stroma have high fiber alignment due to the presence of blood vessels, which cause the collagen fibers to align therein. When compared to corresponding position 210 of FIG. 1, the PS-OCT image shows high local retardance at the anterior stroma because image 205 is significantly lighter in shade at position 210, as compared to position 205. In contrast to position 210, position 205 shows low local retardance at the posterior stroma because image 205 is significantly darker in shade. Position 205 of FIG. 1 corresponds to position 265 of FIG. 2, which indicates that the collagen fibers are not aligned in the posterior stroma in the absence of blood vessels. Together, FIGS. 2A and 2B demonstrate that PS-OCT, for instance as described in FIG. 1, may be used to determine certain polarization properties related to the birefringent nature of a sample—here, a porcine iris.

Figure 3A:
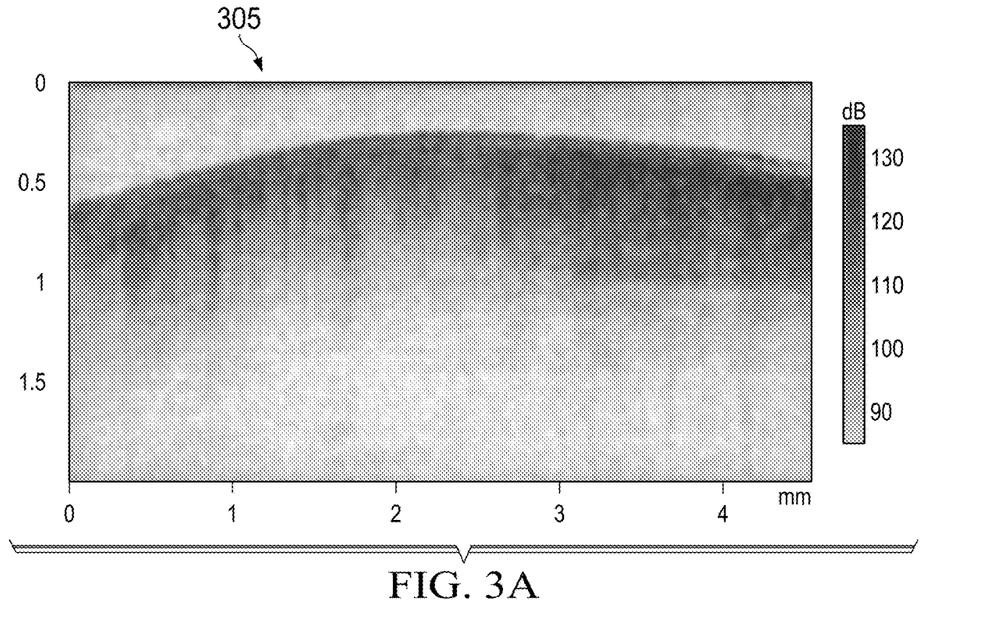
FIG. 3A is a digitally processed image of a chicken tendon generated by non-polarization sensitive OCT.
Figure 3B:
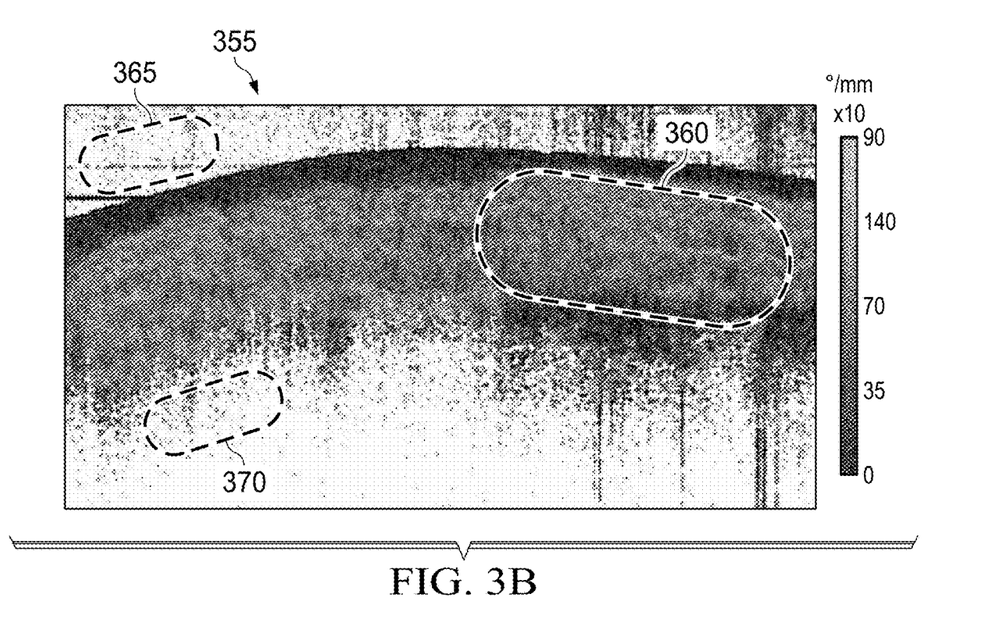
FIG. 3B is a digitally processed image of the same chicken tendon imaged in FIG. 3A, but generated by PS-OCT.

FIG. 3A is a digitally processed image 305 of a chicken tendon generated by non-polarization sensitive OCT, and FIG. 3B is a digitally processed image 355 of the same chicken tendon imaged in FIG. 3A, but generated by PS-OCT. PS-OCT image 355 demonstrates significant contrast between tissues with high fiber alignment, such as the tendon at position 360, and tissues with low fiber alignment, such as the connective tissues above the tendon at position 365 and below at position 370. In contrast, because OCT image 305 only accounts for reflective intensity and not polarization, it presents significantly less contrast between tissues with high fiber alignment and tissues with low fiber alignment.

Figure 4A:
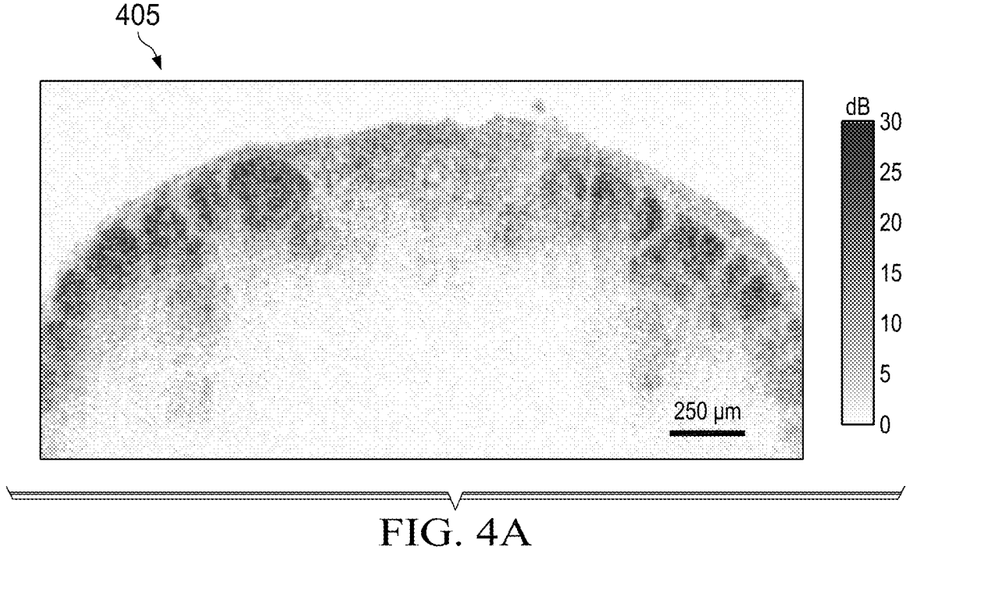
FIG. 4A is digitally processed image of a mouse tail generated by non-polarization sensitive OCT.
Figure 4B:
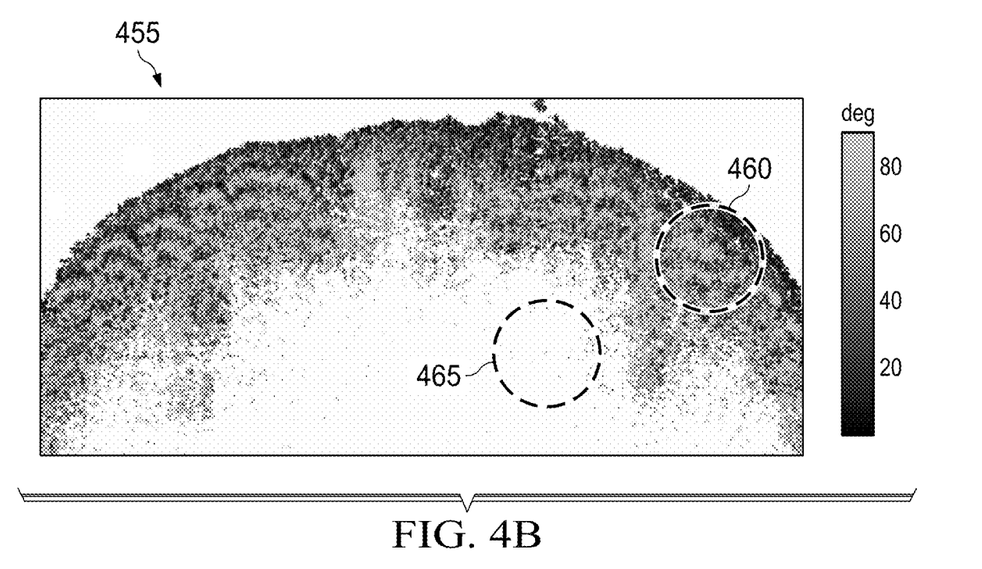
FIG. 4B is a digitally processed image of the same mouse tail imaged in FIG. 4A, but generated by PS-OCT.

FIG. 4A is digitally processed image 405 of a mouse tail generated by non-polarization sensitive OCT, and FIG. 4B is a digitally processed image 455 of the same mouse tail, but generated by PS-OCT. In contrast to OCT image 405, PS-OCT image 455 clearly shows a banding pattern that is due to tissue birefringence. Specifically, the tendons at position 460 have high fiber alignment and accordingly are highly birefringent. The tendons at position 460 appear as bright structures to the side of an artery in the middle, at position 465. The comparison of OCT image 405 and PS-OCT image 455 demonstrates that PS-OCT provides greater tissue discrimination and additional information regarding the tissue, in relation to non-polarization sensitive OCT.

Figure 5A:
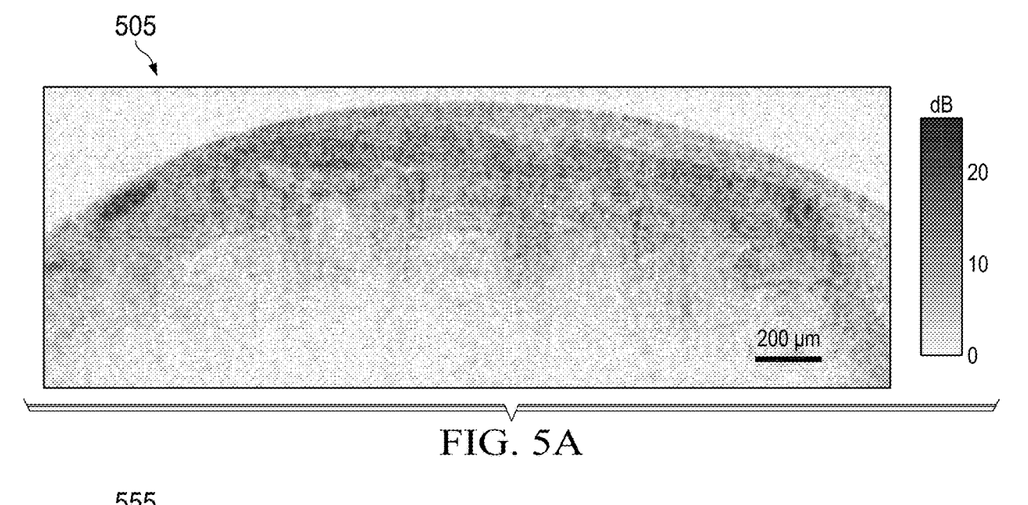
FIG. 5A is a digitally processed image of an exposed mouse foot generated by non-polarization sensitive OCT.
Figure 5B:
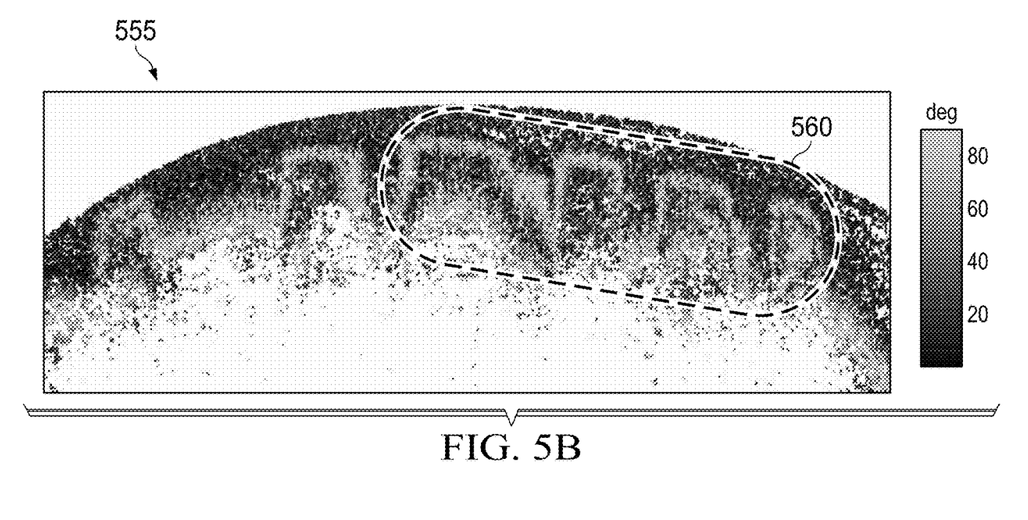
FIG. 5B is a digitally processed image of the same exposed mouse foo imaged in FIG. 5A, but generated by PS-OCT.

FIG. 5A is a digitally processed image 505 of an exposed mouse foot generated by non-polarization sensitive OCT, and FIG. 5B is a digitally processed image 555 of the same exposed mouse foot, but generated by PS-OCT. In contrast to OCT image 505, PS-OCT image 555 clearly shows a banding pattern that is due to tissue birefringence of the extensor tendons of the mouse foot. Specifically, the extensor tendons 560 have high fiber alignment and accordingly are highly birefringent. These extensor tendons are not readily discerned in OCT image 505. Thus, a comparison of OCT image 505 and PS-OCT image 555 also demonstrates that PS-OCT provides greater tissue discrimination and additional information regarding the tissue, in relation to non-polarization sensitive OCT.

Figure 6:
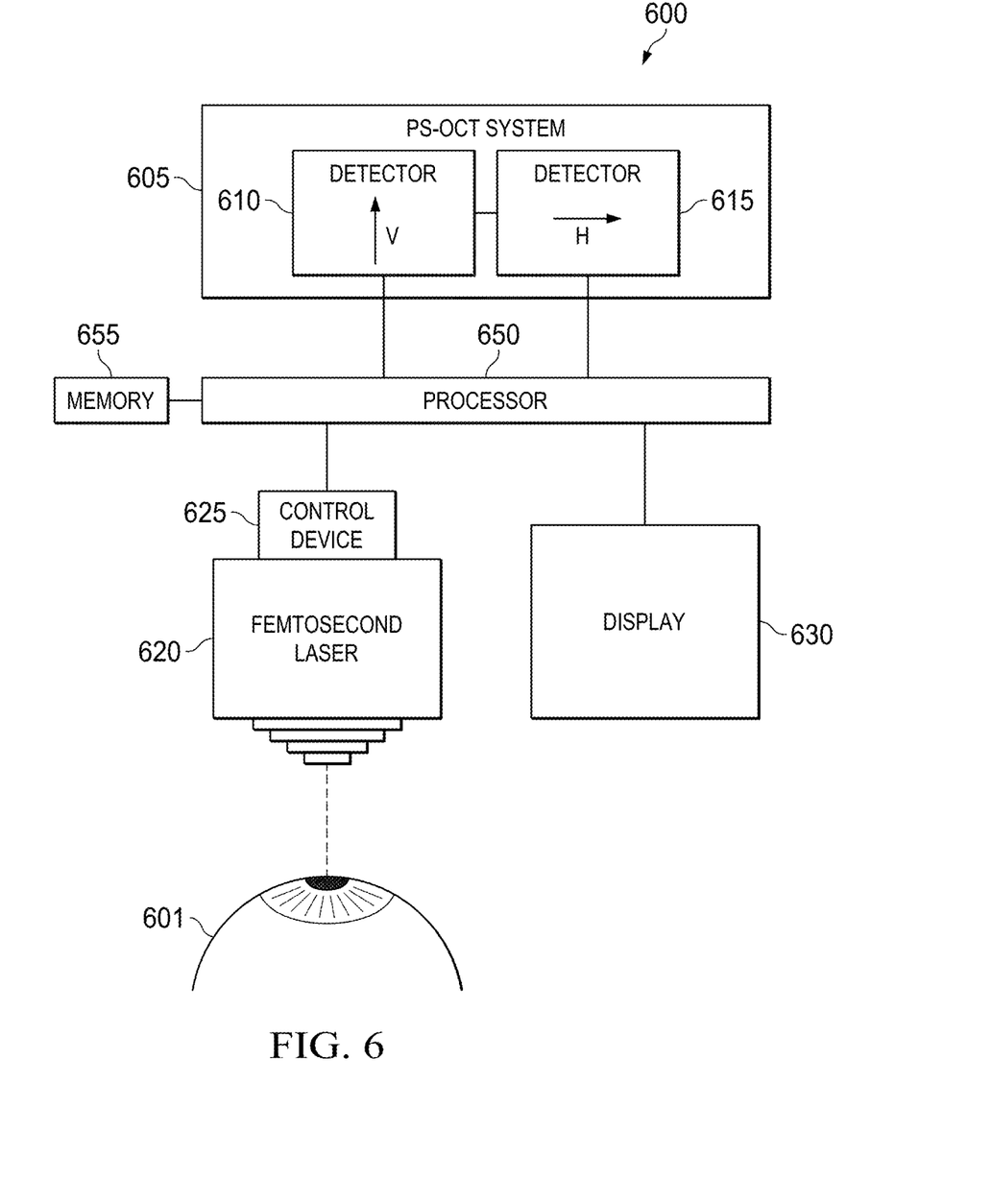
FIG. 6 schematic diagram of a system for cutting a flap in laser ophthalmic surgery using PS-OCT.

FIG. 6 is a schematic diagram of a system 600 for cutting a flap in laser ophthalmic surgery using PS-OCT. System 600 includes a PS-OCT system 605, which is connected to processor 650 and memory 655. Processor 650 is also connected to femtosecond laser 620 via control device 625, which may adjust the photodisruption pattern generated by the femtosecond laser. Femtosecond laser 620 can generate a photodisruption pattern to cut a flap on the sample. As shown, processor 650 is also connected to display 630. PS-OCT system 605 may be identical to the PS-OCT system 100 described in FIG. 1, or may be a similar PS-OCT system with additional, fewer, or substituted components. In FIG. 6, though not shown, PS-OCT system 605 includes a PS-OCT light source, polarization component, beam splitter, polarization system (here, a QWP at 22.5 degrees), reference reflector, a wave plate (here, a QWP at 45 degrees), and a PBS. The polarization component controls the polarization of the PS-OCT source beam. PS-OCT system 605 also includes vertical polarization sensitive detector 610 and horizontal polarization sensitive detector 615, which are both connected to processor 650.

As described in FIG. 1, the PS-OCT light source generates a PS-OCT source beam, which is propagated through the polarization component, to the beam splitter. The polarization component receives the incident PS-OCT source beam and transmits a polarized PS-OCT source beam with a known polarization. At the beam splitter, the polarized PS-OCT source beam is split into two component beams, a polarized sample beam that is propagated to and at least partially reflected by a sample, and a polarized reference beam that is propagated to and reflected by a reference reflector. The sample beam may be referred to as propagated on the sample arm, and the reference beam may be referred to as propagated on the reference arm.

On the sample arm, in FIG. 6, before reaching the sample, the sample beam passes through a wave plate (here, a QWP at 45 degrees), which converts the sample beam into polarized light with a known polarization state such that a polarized sample beam is incident upon the sample. Similarly, on the reference arm, before reaching the reference reflector, the reference beam passes through a polarization system (here, a QWP at 22.5 degrees), which converts the polarization state of the returning reference beam into a polarization state with two equal orthogonal polarization components. In other examples, depending on the configuration of the PS-OCT system, a polarization system may not be implemented. Each of these component beams (the sample beam and the reference beam) are typically reflected back to the beam splitter and combined, although certain PS-OCT systems may not require each reflected beam to return to the beam splitter to be combined.

When the reflected sample beam and the reflected reference beam are combined at the beam splitter, they form a reflected PS-OCT beam, which is directed to the PBS. At the PBS the reflected PS-OCT beam is split into a component that is vertically polarized and directed to vertical polarization sensitive detector 610, and a component that is horizontally polarized and directed to horizontal polarization sensitive detector 615. Though described as a dual-detector system, system 600 may be configured as a single-detector system, in which the single-detector detects both reflected PS-OCT light that is vertically polarized and horizontally polarized. A single-detector system may include a combined horizontal polarization sensitive and vertical polarization sensitive detector. As shown in FIG. 6, detectors 410 and 415 each generate data relating to the interference pattern of the reflected PS-OCT beam and transmit that data to processor 650.

Processor 650 may process the data to determine certain polarization properties of the portion of the sample reflecting the sample beam, such as the relative fiber orientation, based on the birefringence properties of the portion of the sample, eye 601. Processor 650 may further determine whether the photodisruption pattern generated by the femtosecond laser 620 should be adjusted horizontally or vertically based on the relative fiber orientation of the portion of the sample reflecting the sample beam. As used herein with respect to an eye, "horizontal" refers to the X and Y-directions in the X-Y plane, defined as the plane roughly perpendicular to the apex of the cornea, and "vertical" refers to the Z-direction in the Z-plane, defined as the plane roughly perpendicular to the X-Y plane. Processor 650 may generate a control signal to adjust the photodisruption pattern generated by the femtosecond laser 620 horizontally or vertically, when it is determined that the photodisruption pattern should be adjusted. This control signal may be transmitted to control device 625 to adjust the photodisruption pattern.

As described above, when cutting a flap on the cornea, it is important to preserve the biomechanical integrity and stability of the cornea to minimize trauma to the tissue and facilitate post-operative healing with minimal or no intervention. System 600 may control or adjust the depth or shape of the flap by adjusting the photodisruption pattern at which the flap is cut by using the data generated by PS-OCT system 605. Processor 650 may generate a control signal to adjust the depth or shape of the flap by adjusting the photodisruption pattern generated by the femtosecond laser, when it is determined that the photodisruption pattern should be adjusted, and transmit the control signal to the control device 625 of femtosecond laser 620. In one example, the processor may be further configured to determine whether the relative fiber orientation is lower than a user-specified threshold, and to generate the control signal to adjust the photodisruption pattern when the relative fiber orientation is lower than the user-specified threshold. In another example, the processor may be further configured to determine the relative fiber density of the portion of the sample reflecting the sample beam, based on the birefringence properties of the portion of the sample, determine whether the relative fiber density is lower than a user-specified threshold, and generate the control signal to adjust the photodisruption pattern when the relative fiber density is lower than the user-specified threshold. In both of these examples, the control signal to adjust the photodisruption pattern does not cause the depth of the flap to be less than a user-specified minimum depth required to create a functional flap.

Figure 7:
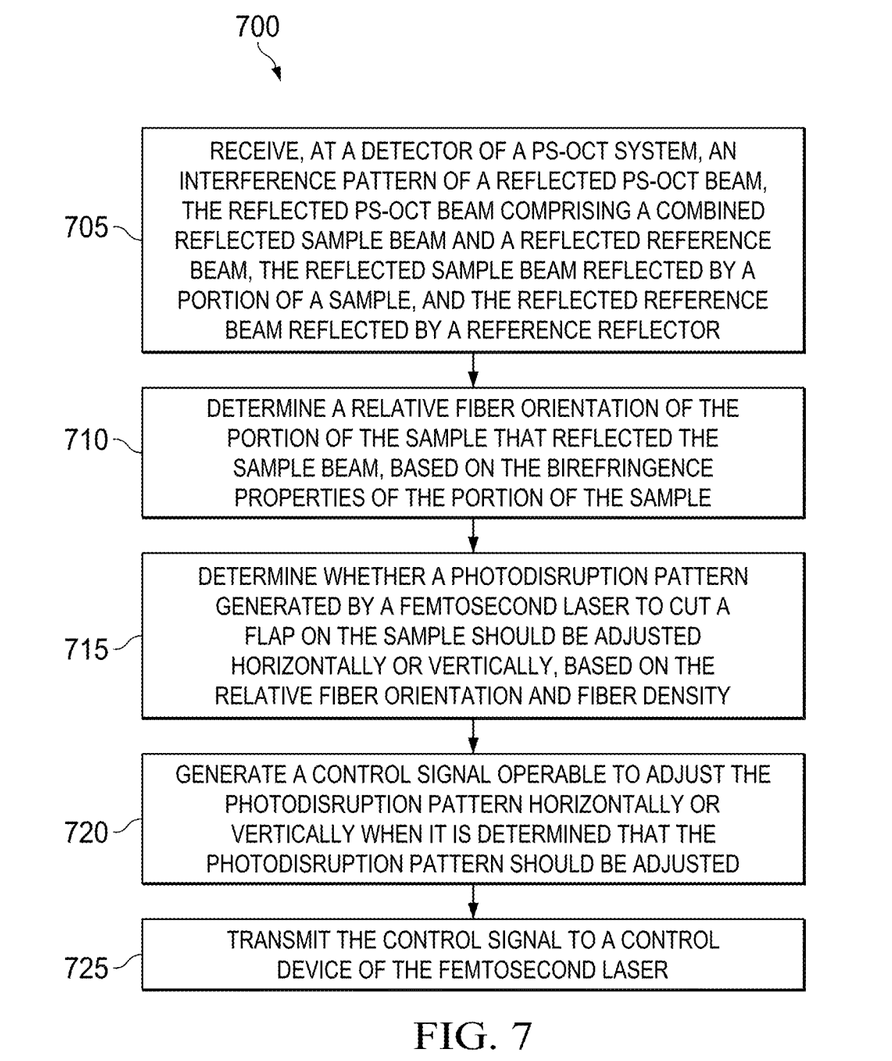
FIG. 7 is a flowchart of a method for cutting a flap in the cornea of an eye during ophthalmic surgery using PS-OCT.

By adjusting the depth of the flap cut or adjusting the shape of the flap cut, by adjusting the photodisruption pattern in places where the fiber alignment is less than measured, calculated, or anticipated, method 700 may optimize the flap cut, thereby preserving the biomechanical integrity and stability of the corneal tissue. In another example, system 600 may also optimize the flap cut to account for acute inaccuracies that may arise during the procedure, for instance eye rotation or changes in patient positioning.

In system 600, processor 650 may be further configured to use the data to generate a pictorial representation of the tissue at the portion of the eye that reflected the sample beam. Pictorial representations may be presented on display 630, which may be a display screen or a head-up display. Such pictorial representations indicate the fiber orientation of the corneal tissue based on birefringence of the corneal tissue. Because the fiber orientation of the corneal tissue affects the polarization of incident light (the sample beam), at least via birefringence, the phase retardation of the reflected sample beam may be determined as a function of tissue depth. Generally, birefringence of tissue increases as fiber orientation increases, and as a result, the phase retardation of the reflected sample beam will differ as compared to the reflected reference beam.

Data generated by the PS-OCT system of system 600 may be used pre-operatively to assess whether the patient is a good candidate for laser treatment. Such data may further be used to examine characteristics of the cornea to determine the depth of the cut required to create a functional flap, and to determine places where the depth of the flap may be or should be varied to compensate for increased risk of post-surgical complications and difficulty healing due to physical trauma upon the corneal tissue. Data generated pre-operatively may be used during the procedure to confirm that significant parameters of the eye have not changed since the pre-operative analysis such that the patient is no longer a good candidate for laser treatment. Post-operatively, prior PS-OCT images (those generated pre-operatively and during the procedure) may be compared to subsequently generated PS-OCT images to evaluate whether the cornea is healing properly.

A processor 650 may include, for example a microprocessor, microcontroller, digital signal processor (DSP), application specific integrated circuit (ASIC), or any other digital or analog circuitry configured to interpret and/or execute program instructions and/or process data. In some embodiments, processor 650 may interpret and/or execute program instructions and/or process data stored in memory 655. Memory 655 may be configured in part or whole as application memory, system memory, or both. Memory 655 may include any system, device, or apparatus configured to hold and/or house one or more memory modules. Each memory module may include any system, device or apparatus configured to retain program instructions and/or data for a period of time (e.g., computer-readable media). The various servers, electronic devices, or other machines described may contain one or more similar such processors or memories for storing and executing program instructions for carrying out the functionality of the associated machine.

FIG. 7 is a flowchart of a method 700 for cutting a flap in laser ophthalmic surgery using PS-OCT. At step 705, an interference pattern of a reflected PS-OCT beam is received at a detector of a PS-OCT system. The reflected PS-OCT beam includes a combined reflected sample beam and reflected reference beam. The reflected sample beam is reflected by a portion of a sample, and the reflected reference beam is reflected from a reference reflector of the PS-OCT system. The sample may be a biological tissue. As described in FIG. 7, the sample is a human eye. The detector in step 705 may be a single or dual-detector system. A dual-detector system includes a vertical polarization sensitive detector and a horizontal polarization sensitive detector, and the PS-OCT system may further include a polarizing beam splitter that splits the reflected PS-OCT beam into a vertically polarized component and a horizontally polarized component, the vertically polarized component directed to the vertical polarization sensitive detector, and the horizontally polarized component directed to the horizontal polarization sensitive detector. A single-detector system may include a combined horizontal polarization sensitive and vertical polarization sensitive detector.

At step 710, the relative fiber orientation of the portion of the sample that reflected the sample beam is determined, based on the birefringence properties of the portion of the sample reflecting the sample beam. Because the fibers of the eye tissue reflecting the sample beam are birefringent, any change in polarization of the sample beam after contacting the sample provides information as to the polarization properties of that tissue, for instance, fiber orientation and fiber. Generally, tissue birefringence increases as fiber orientation increases, and as a result, the phase retardation of the reflected sample beam will differ as compared to the reflected reference beam.

At step 715, whether a photodisruption pattern generated by a femtosecond laser to cut a flap on the sample should be adjusted horizontally or vertically is determined, based on the relative fiber orientation of the portion of the sample that reflected the sample beam. By adjusting the photodisruption pattern generated by the femtosecond laser, method 700 may adjust the depth of the flap cut or the shape of the flap cut based on the relative fiber orientation determined at step 710. For example, if it is determined that the fiber orientation of a particular section of the eye is weak or otherwise compromised, it may be determined that the photodisruption pattern should be adjusted to decrease the depth of the flap overall or only in one section, or to adjust the shape of the flap to cut around the weak or compromised section.

At step 720, a control signal is generated to adjust the photodisruption pattern by adjusting the femtosecond laser via a control device connected to the femtosecond laser, the control device able to adjust the photodisruption pattern generated by the femtosecond laser, when it is determined that the photodisruption pattern should be adjusted at step 715. In this example, the control signal to adjust the photodisruption pattern does not cause the depth of the flap to be less than a user-specified minimum depth required to create a functional flap, regardless of whether the depth or shape of the flap cut is adjusted by the photodisruption pattern. At step 725, the control signal may transmitted to a control device connected to the femtosecond laser to adjust the photodisruption pattern.

For example, if it is determined at step 710 that the fiber orientation of the tissue differs from certain user-defined parameters, and at step 715 that the photodisruption pattern should be adjusted, the control device connected to the femtosecond laser may be configured to adjust the photodisruption pattern in real time. In this example, it may be determined during the flap cutting procedure that the tissue has relatively low fiber alignment, such that there is significant risk to the biomechanical stability of the corneal tissue. In these situations, the depth of the flap may be adjusted to the minimal depth required to still create a functional flap. In another example, the depth of the flap may be optimized to account for acute inaccuracies that may arise during the procedure, for instance eye rotation or changes in patient positioning. Further, for example, if it is determined at step 710 that the fiber orientation of the tissue differs from certain user-defined parameters, alternatively or in addition to adjusting the depth of the flap, the femtosecond laser may be configured to adjust the photodisruption pattern in real time, which may cause the depth or shape of the flap to be adjusted in real time. By adjusting the depth or shape of the flap, by adjusting the photodisruption pattern, the femtosecond laser may avoid sections of tissue in which a significant risk to the biomechanical stability of the corneal tissue is detected, thus optimizing the flap while it is being created.

In one example, method 700 may further include determining whether the relative fiber orientation is lower than a user-specified threshold, and generating the control signal to adjust the photodisruption pattern when the relative fiber orientation is lower than the user-specified threshold. In another example, method 700 may also include determining whether the relative fiber orientation or fiber density is lower than a user-specified threshold, and generating the control signal to adjust the photodisruption pattern when the relative fiber orientation or fiber density is lower than the user-specified threshold. In both of these examples, the control signal to adjust the photodisruption pattern does not cause the depth of the flap to be less than a user-specified minimum depth required to create a functional flap.

Method 700 may further include generating a pictorial representation of the portion of the sample that reflected the sample beam, and transmitting the pictorial representation to a display. Such a pictorial representation may be a digitally processed PS-OCT image, for example, as shown in FIG. 2A, FIG. 3B, FIG. 4B, or FIG. 5B.

Method 700 may be implemented in the systems of FIG. 1 or FIG. 6, or any other suitable system. The preferred initialization point for such methods and the order of their steps may depend on the implementation chosen. In some embodiments, some steps may be optionally omitted, repeated, or combined. In some embodiments, some steps of such methods may be executed in parallel with other steps. In certain embodiments, the methods may be implemented partially or fully in software embodied in computer-readable media.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A system for cutting a flap in the cornea of an eye using polarization sensitive optical coherence tomography (PS-OCT), the cornea having a stroma constructed of collagen fibers, the system comprising:
   a PS-OCT system comprising:
      a PS-OCT source operable to generate a PS-OCT source beam;
      a polarization component operable to control a polarization of the PS-OCT source beam;
      a reference reflector;
      a beam splitter operable to split the PS-OCT source beam into a sample beam that travels along a sample arm until it is reflected by the stroma of the cornea of the eye to form a reflected sample beam, and a reference beam that travels along a reference arm until it is reflected by the reference reflector to form a reflected reference beam, and operable to combine the reflected sample beam and the reflected reference beam to form a reflected PS-OCT beam;
      a wave plate operable to convert the sample beam into polarized light with a known polarization state such that a polarized sample beam is incident upon the sample;
      a detector operable to receive the reflected PS-OCT beam, detect an interference pattern of the reflected PS-OCT beam, and generate data relating to the interference pattern; and
   a femtosecond laser operable to generate a photodisruption pattern to cut a flap in the cornea, and connected to a control device operable to adjust the photodisruption pattern generated by the femtosecond laser; and
   a processor programmed to:
      receive data relating to the interference pattern of the reflected PS-OCT beam;
      determine a relative collagen fiber orientation and collagen fiber density of the portion of the stroma reflecting the sample beam, based on a birefringence properties of the portion of the stroma, wherein the relative collagen fiber orientation comprises a location of strong collagen fiber alignment and a location of weak collagen fiber alignment in the portion of the stroma, the location of strong fiber alignment having collagen fibers that are more aligned with each other than collagen fibers in the location of weak collagen fiber alignment, and wherein the relative collagen fiber density comprises a location of strong collagen fiber density and a location of weak collagen fiber density in the portion of the stroma, the location of strong fiber density having collagen fibers that are denser than collagen fibers in the location of weak collagen fiber density;
      determine whether the photodisruption pattern should be adjusted based on the collagen fiber orientation or collagen fiber density of the portion of the sample by determining the location of strong collagen fiber alignment and the location of weak collagen fiber alignment or weak collagen fiber density;
      generate a control signal operable to adjust the photodisruption pattern so that the photodisrutpion pattern is located at the location of strong collagen fiber alignment and minimizing a depth of the cut at the location of weak collagen fiber alignment or weak collagen fiber density; and
      transmit the control signal to the control device connected to the femtosecond laser.

2. The system of claim 1, wherein the polarization component is a vertical polarizer or a horizontal polarizer.

3. The system of claim 1, wherein the detector is a dual-detector system comprising a vertical polarization sensitive detector and a horizontal polarization sensitive detector, and wherein the system further comprises
   a polarizing beam splitter operable to split the reflected PS-OCT beam into a vertically polarized component and a horizontally polarized component, the vertically polarized component directed to the vertical polarization sensitive detector, and the horizontally polarized component directed to the horizontal polarization sensitive detector.

4. The system of claim 1, wherein the detector is a single-detector system comprising a combined horizontal polarization sensitive and vertical polarization sensitive detector.

5. The system of claim 1, wherein the processor is further programmed to determine whether the relative fiber orientation is lower than a user-specified threshold, and generate the control signal to adjust the photodisruption pattern when the relative fiber orientation is lower than the user-specified threshold.

6. The system of claim 5, wherein the control signal to adjust the photodisruption pattern does not cause the depth of the flap to be less than a user-specified minimum depth required to create a functional flap.

7. The system of claim 1, wherein the processor is further programmed to:
determine a relative fiber density of the portion of the sample reflecting the sample beam, based on the birefringence properties of the portion of the sample;
determine whether the relative fiber density is lower than a user-specified threshold; and
generate the control signal to adjust the photodisruption pattern when the relative fiber density is lower than the user-specified threshold.

8. The system of claim 7, wherein the control signal to adjust the photodisruption pattern does not cause the depth of the flap to be less than a user-specified minimum depth required to create a functional flap.

9. The system of claim 1, wherein the processor is further programmed to generate and transmit a pictorial representation of the portion of the sample reflecting the sample beam; and
wherein the system further comprises a display operable to present the pictorial representation.

10. A method for cutting a flap on an eye using polarization sensitive optical coherence tomography (PS-OCT), comprising:
receiving, at a detector of a PS-OCT system, an interference pattern of a reflected PS-OCT beam, the reflected PS-OCT beam comprising a combined reflected sample beam and a reflected reference beam, the reflected sample beam reflected by a portion of a stroma in a cornea of an eye, and the reflected reference beam reflected by a reference reflector;
determining a relative collagen fiber orientation and collagen fiber density of the portion of the stroma reflecting the sample beam, based on a birefringence properties of the portion of the stroma, wherein the relative collagen fiber orientation comprises a location of strong collagen fiber alignment and a location of weak collagen fiber alignment in the portion of the stroma, the location of strong fiber alignment having collagen fibers that are more aligned with each other than collagen fibers in the location of weak collagen fiber alignment, and wherein the relative collagen fiber density comprises a location of strong collagen fiber density and a location of weak collagen fiber density in the portion of the stroma, the location of strong fiber density having collagen fibers that are denser than collagen fibers in the location of weak collagen fiber density;
determining whether a photodisruption pattern generated by a femtosecond laser to cut a flap in the stroma should be adjusted, based on the polarization properties of the portion of the stroma by determining a location of strong collagen fiber alignment and a location of weak collagen fiber alignment or weak collagen fiber density; and
controlling the photodisruption pattern so that the photodisrutpion pattern is located at the location of strong collagen fiber alignment and minimizing a depth of the cut at the location of weak collagen fiber alignment or weak collagen fiber density.

11. The method of claim 10, wherein the detector of the PS-OCT system is a dual-detector system comprising a vertical polarization sensitive detector and a horizontal polarization sensitive detector, and wherein the PS-OCT system further comprises
a polarizing beam splitter operable to split the reflected PS-OCT beam into a vertically polarized component and a horizontally polarized component, the vertically polarized component directed to the vertical polarization sensitive detector, and the horizontally polarized component directed to the horizontal polarization sensitive detector.

12. The method of claim 10, wherein the detector of the PS-OCT system is a single-detector system comprising a combined horizontal polarization sensitive and vertical polarization sensitive detector.

13. The method of claim 10, further comprising:
determining whether the relative fiber orientation is lower than a user-specified threshold; and
generating the control signal to adjust the photodisruption pattern when the relative fiber orientation is lower than the user-specified threshold.

14. The method of claim 13, wherein the control signal to adjust the photodisruption pattern does not cause the depth of the flap to be less than a user-specified minimum depth required to create a functional flap.

15. The method of claim 10, further comprising:
determining a relative fiber density of the portion of the sample reflecting the sample beam, based on the birefringence properties of the portion of the sample;
determining whether the relative fiber density is lower than a user-specified threshold; and
generating the control signal to adjust the photodisruption pattern when the relative fiber density is lower than the user-specified threshold.

16. The method of claim 15, wherein the control signal to adjust the photodisruption pattern does not cause the depth of the flap to be less than a user-specified minimum depth required to create a functional flap.

17. The method of claim 10, further comprising:
generating a pictorial representation of the portion of the sample that reflected the sample beam; and
transmitting the pictorial representation to a display.

* * * * *